US006160108A

United States Patent [19]
Reed et al.

[11] Patent Number: 6,160,108
[45] Date of Patent: Dec. 12, 2000

[54] PLATELET ACTIVATION PROTEIN

[75] Inventors: Guy Reed, Winchester; Christophe Y. Clement, Cambridge, both of Mass.

[73] Assignee: President and Fellows of Harvard College, Cambridge, Mass.

[21] Appl. No.: 08/725,758

[22] Filed: Oct. 4, 1996

Related U.S. Application Data

[60] Provisional application No. 60/005,074, Oct. 6, 1995.

[51] Int. Cl.$^7$ .......................... C07H 21/04; C12N 15/63; C12N 5/10
[52] U.S. Cl. .......................... 536/23.5; 435/6; 435/320.1; 435/352.3; 435/325
[58] Field of Search ..................... 536/23.5; 435/320.1, 435/6, 352.3, 352.33, 325

[56] References Cited

U.S. PATENT DOCUMENTS 5,446,132   8/1995   Reed et al. ............................... 530/350

OTHER PUBLICATIONS

Biodirectory '96, Piscataway, by Phamacia Biotech, p. 131, 1996.
Amthauer et al., "Placental Alkaline Phosphatase: A Model for Studying COOH–Terminal Processing of Phosphatidylinositol–Glycan–Anchored Membrane Proteins", *Clin. Chem.*, 38:2510–16 (1992).
Bennett, "The Molecular Biology of Platelet Membrane Proteins", *Seminars in Hematology*, 27:186–204 (1990).
Berman et al., "A Platelet Alpha Granule Membrane Protein That Is Associated with the Plasma Membrane After Activation", *J. Clin. Invest.*, 78:130–137 (1986).
Coller, "A New Murine Monoclonal Antibody Reports an Activation–dependent Change in the Conformation and/or Microenvironment of the Platelet Glycoprotein IIb/IIIa Copmlex", *J. Clin. Invest.*, 76:101–108 (1985).
Einfeld et al., "Transport of Membrane Proteins to the Cell Surface", *Curr. Topics Microbiol. Immunol.*, 170:107–39 (1991).
Febbraio et al., "Identification and Characterization of LAMP–1 as an Activation–dependent Platelet Surface Glycoprotein", *J. Biol. Chem.*, 265:18531–18537 (1990).
Feinberg et al., Addendum: "A Technique for Radiolabeling DNA Restriction Endonuclease Fragments to High Specific Activity", *Anal. Biochem.*, 137:266–67 (1984).
Foley et al., "Continuous Culture Of Human Lymphoblasts From Peripheral Blood Of A Child With Acute Leukemia", *Cancer*, 18:522–529 (1965).
Fox et al., "Poly(A) Addition During Maturation of Frog Oocytes: Distinct Nuclear and Cytoplasmic Activities and Regulation by the Sequence UUUUUAU", *Genes & Dev.*, 3:2151–62 (1989).
Fraker et al., "Protein and Cell Membrane Iodinations With a Sparingly Soluble Chloroamide, 1,3,4,6–Tetrachloro–3a, 6a–Diphenylglycoluril", *Biochem. Biophys. Res. Commun.*, 80:849–57 (1978).

Fugman et al., "In Vitro Establishment and Characterization of a Human Megakaryoblastic Cell Line", *Blood*, 75:1252–1261 (1990).
Gish et al., "Identification of Protein Coding Regions by Database Similarity Search", *Nat. Genet.*, 3:266–72 (1993).
Grange et al., "Human mRNA Polyadenylate Binding Protein: Evolutionary Conservation of a Nucleic Acid Binding Motif", *Nucleic Acids Res.*, 15:4771–4787 (1987).
Greenberg et al., "Characterization of a New Megakaryocytic Cell Line: The Dami Cell", *Blood*, 72:1968–1977 (1988).
Hamburger et al., "GMP–140 Mediates Adhesion of Stimulated Platelets to Neutrophils", *Blood*, 75:550–554 (1990).
Hayward et al., "A Novel, Multimeric Platelet Protein that is Released with Platelet Activation and Expressed on the Surface of Activated Platelets", *Blood*, 76 (Suppl 1) 458A:P–155 (1990).
Houng et al., "A Novel Platelet–Cell Activated Protein", *Circulation, Abstracts from the 67th Scientific Sessions*, vol. 90, p. I–31, Abstract No. 0699 (1994).
Johnston et al., "Cloning of GMP–140, a Granule Membrane Protein of Platelets and Endothelium: Sequence Similarity to Proteins Involved in Cell Adhesion and Inflammation", *Cell*, 56:1033–44 (1989).
Kennedy et al., "Protein–Protein Coupling Reactions and the Applications of Protein Conjugates", *Clin. Chim. Acta.* 70:1–31 (1976).
Khyse–Anderson, "Electroblotting of Multiple Gels: A Simple Apparatus Without Buffer Tank for Rapid Transfer of Proteins from Polyacrylamide to Nitrocellulose", *J. Biochem. Biophys. Meth.*, 10:203–209 (1984).
Kozak, "The Scanning Model for Translation: An Update", *J. Cell. Biol.*, 108:229–41 (1989).
Larsen et al., "Padgem Protein: A Receptor That Mediates the Interaction of Activated Platelets with Neutrophils and Monocytes", *Cell*, 59:305–312 (1989).
Lefrère et al., "Drosophila Melanogaster Poly(A)–binding Protein: cDNA Cloning Reveals an Usually Long 3'–untranslated Region of the mRNA, also Present in Other Eukaryotic Species", *Gene*, 96:219–225 (1990).
Lin et al., "A Platelet Membrane Protein Expressed During Platelet Activation and Secretion", *J. Bio. Chem.*, 259:9121–26 (1984).
Lukacova et al., "Single Step Purification of Platelet Factor XIII Using an Immobilized Factor XIII A–Subunit Monoclonal Antibody", *Thromb. Haemostas.*, 69:397–400 (1993).
Lukacova et al., "Inhibition of Factor XIII Activation by an Anti–Peptide Monoclonal Antibody" *Biochemistry*, 30:10164–10170 (1991).

(List continued on next page.)

*Primary Examiner*—David Saunders
*Assistant Examiner*—Mary Beth Tung
*Attorney, Agent, or Firm*—Mintz, Levin, Cohn, Ferris, Glovsky and Popeo, P.C.; Ingrid A. Beattie

[57] ABSTRACT

A substantially pure platelet activation polypeptide including a sequence at least 70% identical to SEQ ID NO:1, and a DNA encoding such a polypeptide.

23 Claims, 7 Drawing Sheets

OTHER PUBLICATIONS

McEver et al., "A Monoclonal Antibody to a Membrane Glycoprotein Binds Only to Activated Platelets", *J. Biol. Chem.*, 259:9799–804 (1984).

McGrew et al., "Poly(A) Elongation During Xenopus Oocyte Maturation is Required for Translational Recruitment and is Mediated by a Short Sequence Element", *Genes Dev.*, 3:803–15 (1989).

Mudgett–Hunter et al., "Binding and Structural Diversity Among High–Affinity Monoclonal Anti–Digoxin Antibodies", *Mol. Biol.*, 22:477–88 (1985).

Munson et al., "Ligand: A Versatile Computerized Approach for Characterization of Ligand–Binding Systems", *Anal. Biochem.*, 107:220–39 (1980).

Mustard et al., "Isolation of Human Platelets from Plasma by Centrifugation and Washing", *Meth. Enzymol.*, 169(1):3–11 (1989).

Nietfeld et al., "The Xenopus laevis poly(A) Binding Protein is Composed of Multiple Functionally Independent RNA Binding Domains", *EMBO J.*, 9:3699–3705 (1990).

Reed et al., "Characterization of APP: A Protein Expressed on the Platelet Membrane after Cellular Activation", *Circulation, Abstracts from the 66th Scientific Sessions*, p. I–457, Abstract No. 2459 (1993).

Reed et al., "Acceleration of Plasma Clot Lysis by an Antibody to $\alpha_2$–Antiplasmin", *Trans. Assoc. Am. Phys.*, 101st Session, D.C., vol. C1:250–256 (1988).

Runge et al., "Paramagnetic NMR Contrast Agents Development and Evaluation", *Invest. Radiol.* 19:408–15 (1984).

Sachs et al., "A Single Gene From Yeast for Both Nuclear and Cytoplasmic Polyadenylate–Binding Proteins: Domain Structure and Expression", *Cell*, 45:827–835 (1986).

Sachs et al., "A Single Domain of Yeast Poly(A)–Binding Protein is Necessary and Sufficient for RNA Binding and Cell Viability", *Mol. Cell. Biol.*, 7:3268–76 (1987).

Sandoval et al., "Targeting of Membrane Proteins to Endosomes and Lysosomes", *Trends Cell Biol.*, 4:292–297 (1994).

Savage et al., "Thrombin–Induced Increase in Surface Expression of Epitopes on Platelet Membrane Glyco–protein IIb/IIIa Complex and GMP–140 Is a Function of Platelet Age", *Blood*, 74:1007–14 (1989).

Schaefer et al., "In Vivo Nuclear Magnetic Resonance Imaging of Myocardial Perfusion Using the Paramagnetic Contrast Agent Manganese Gluconate", *JACC*, 14:472–80 (1989).

Schuurs et al., "Enzyme–Immunoassay", *Clin. Chim. Acta.* 81:1–40 (1977).

Shreve et al., "Monoclonal Antibodies Labeled with Polymeric Paramagnetic Ion Chelates", *Magn. Reson. Med.*, 3:336–40 (1986).

Singer et al., "The Fluid Mosaic Model of the Structure of Cell Membranes", *Science*, 175:720–31 (1972).

Stambuck et al. "Purification and Characterization of Recombinant Xenopus poly(A) ± Binding Protein Epxressed in a Baculovirs System", *Biochem. J.*, 287:761–766 (1992).

Stenberg et al., "A Platelet Alpha–Granule Membrane Protein (GMP–140) Is Expressed on the Plasma Membrane after Activation", *J. Cell Biol.*, 101:880–886 (1985).

Tian et al., "A Polyadenylate Binding Protein Localized to the Granules of Cytolytic Lymphocytes Induces DNA Fragmentation in Target Cells", *Cell*, 67:629–639 (1991).

Timmons et al., "Isolation of Human Platelets by Albumin Gradient and Gel Filtration", *Methods in Enzymology*, 169:11–12 (1989).

Wang et al., "Nucleotide Sequence of a Mouse Testis poly(A) Binding Protein cDNA" *Nucleic Acids Res.*, 20:3519 (1992).

Wesbey et al., "Paramagnetic Pharmaceuticals for Magnetic Resonance Imaging", *Physiol. Chem. Phys. Med. NMR*, 16:145–55 (1984).

Wolf, "Contrast Enhancement in Biomedical NMR", *Physiol. Chem. Phys. Med. NMR*, 16:93–95 (1984).

Zelus et al., "Expression of the Poly(A)–Binding Protein During Development of *Xenopus laevis*", *Mol. Cell. Biol.*, 9:2756–2760 (1989).

| | | | | |
|---|---|---|---|---|
| GCGAGAGGGC | CAGAGGAGAA | AGAGAGAGCG | CGAAAGAGAG | AGGATGTCTC | TCTCAGACTG | 60 |
| GCACCTGGCG | GTGAAGCTGG | CTGACCAGCC | ACTTACTCCA | AAGTCTATTC | TTCGGTTGCC | 120 |
| AGAGACAGAA | CTGGGAGAAT | ACTCGCTAGG | GGGCTATAGT | ATTTCATTTC | TGAAGCAGCT | 180 |
| TATTGCTGGC | AAACTCCAGG | AGTCTGTTCC | AGACCCTGAG | CTGATTGATC | TGATCTACTG | 240 |
| TGGTCGGAAG | CTAAAAGATG | ACCAGACACT | TGACTTCTAT | GGCATTCAAC | CTGGGTCCAC | 300 |
| TGTCCATGTT | CTGCGAAAGT | CCTGGCCTGA | ACCTGATCAG | AAACCGGAAC | CTGTGGACAA | 360 |
| AGTGGCTGCC | ATGAGAGAGT | TCCGGGTGTT | GCACACAGCA | CTGCACAGCA | GCTCCTCTTA | 420 |
| CAGGGAGGCG | GTCTTTAAGA | TGCTCAGCAA | TAAGGAGTCT | CTGGATCAGA | TCATTGTGGC | 480 |
| CACCCCAGGC | CTCAGCAGTG | ACCCTATTGC | TCTTGGGGTT | CTCCAGGACA | AGGACCTCTT | 540 |
| CTCTGTCTTC | GCTGATCCCA | ATATGCTTGA | TACGTTGGTG | CCTGCTCACC | CAGCCCTCGT | 600 |
| CAATGCCATT | GTCCTGGTTC | TGCACTCCGT | AGCAGGCAGT | GCCCCAATGC | CTGGGACTGA | 660 |
| CTCCTCTTCC | CGGAGCATGC | CCTCCAGCTC | ATACCGGGAT | ATGCCAGGTG | GCTTCCTGTT | 720 |
| TGAAGGGCTC | TCAGATGATG | AGGATGACTT | TCACCCAAAC | ACCAGGTCCA | CACCCTCTAG | 780 |
| CAGTACTCCC | AGCTCCCGCC | CAGCCCTCCT | GGGGTACAGT | GGAGCTGCTG | GGCCCCGGCC | 840 |
| CATCACCCAG | AGTGAGCTGG | CCACCGGCCT | GGCCCTGGCC | AGCACTCCGG | AGAGCAGCTC | 900 |
| TCACACACCG | ACTCCTGGCA | CCCAGGGTCA | TCCCTTCAGG | AGCACTCACA | ACCTCACCAA | 960 |
| TGTCCAGTCA | GGGACGCCCA | TCACCAATGA | TCTCTTCAGC | CAAGCCCTAC | AGCATGCCCT | 1020 |
| TCAGGCCTCT | GGGCAGCCCA | GCCTTCAGAG | CCAGTGGCAG | CCCCAGCTGC | AGCAGCTACG | 1080 |
| TGACATGGGC | ATCCAGGACG | ATGAGCTGAG | CTGCGCGGCC | TGCAGGCCAC | CGGTGGGGAC | 1140 |
| ATCCAAGCAG | CCCTGGAGCT | CATCTTTGCT | GGAGGAGCCC | CTGCTTCCCC | CTGCTTCCCC | 1200 |
| TGAACCCCCA | GCAAGTGCA | GAGGCTACTG | CCCTTGGGAG | CATGAACTCC | CATGAAGTTC | 1260 |
| ATCTCTCCCT | TCCCAATAT | ACCTGATGGT | CAACTCTAAA | AAAAAAAAAA | AAAAAAAAA | 1320 |
| ATGAAATACC | ACTACTCTGA | TCGTTTTTC | ACTGACCCCGG | TGAGGCGGCG | CGA | 1373 |

FIG. 4

```
MSLSDWHLAV KLADQPLTPK SILRLPETEL GEYSLGGYSI SFLKQLIAGK LQESVPDPEL    60

IDLIYCGRKL KDDQTLDFYG IQPGSTVHVL RKSWPEPDQK PEPVDKVAAM REFRVLHTAL   120

HSSSSYREAV FKMLSNKESL DQIIVATPGL QDKDLFSVFA DPNMLDTLVP   180

AHPALVNAIV LVLHSVAGSA PMPGTDSSSR SMPSSSYRDM PGGFLFEGLS DDEDDFHPNT   240

RSTPSSSTPS SRPASLGYSG AAGPRPITQS ELATALALAS TPESSSHTPT PGTQGHSSGT   300

SPMSSGVQSG TPITNDLFSQ ALQHALQASG QPSLQSQWQP QLQQLRDMGI QDDELSLRPC   360

RPPVGTSKQP WSSSLLEEPH ELPASPEPPA SCRGYCPWEA LMKVPPSLPS PIYLMVNSKK   420

KKKKKK                                                              426

(SEQ ID NO:2)   FIG. 5
```

FIG. 6

```
GCGAGAGGGC CAGAGGAGAA AGAGAGAGCG CGAAAGAGAG AGGATGTCTC TCTCAGACTG    60
GCACCTGGCG GTGAAGCTGG CTGACCAGCC ACTTACTCCA AAGTCTATTC TTCGGTTGCC   120
AGAGACAGAA CTGGAGAAAT ACTCGCTAGG GGGCTATAGT ATTTCATTTC TGAAGCAGCT   180
TATTGCTGGC AAACTCCAGG AGTCTGTTCC AGACCCTGAG CTGATTGATC TGATCTACTG   240
TGGTCGGAAG CTAAAGATG ACCAGACACT TGACTTCTAT GGCATTCAAC CTGGGTCCAC   300
TGTCCATGTT CTGCGAAAGT CCTGGCCTGA ACCTGATCAG AAACCGGAAC CTGTGACAA   360
AGTGGCTGCC ATGAGAGAGT TCCGGGTGTT GCACACAGCA GCTCCCTCTTA            420
CAGGGAGGCG GTCTTTAAGA TGCTCAGCAA CTGGATCAGA TAAGGAGTCT TCATTGTGGC   480
CACCCCAGGC CTGAGCAGTG ACCCTATTGC TCTTGGGGTT CTCCAGGACA AGGACCTCTT   540
CTCTGTCTTC GCTGATCCCA ATATGCTTGA TACGTTGGTG CCTGCTCACC CAGCCCCTCGT   600
CAATGCCATT GTCCTGGTTC TGCACTCCGT AGCAGGCAGT GCCCCAATGC CTGGGACTGA   660
CTCCTCTTCC CGGAGCATGC CCTCCCAGCTC ATACCGGGAT ATGCCAGGTG GCTTCCTGTT   720
TGAAGGGCTC TCAGATGATG AGGATGACTT TCACCCAAAC ACCAGGTCCA CACCCTCTAG   780
CAGTACTCCC AGCTCCCGCC CAGCCCTCCCT GGGGTACAGT GGAGCTGCTG GGCCCCGGCC   840
CATCACCCAG AGTGAGCTGG CCACCAGCCT GGCCCTGCCC AGCACTCCGG AGAGCAGCTC   900
TCACACACCG ACTCCTGGCA CCCCAGGGTCA TTCCTCAGGG ACCTCACCAA TGTCCTCTGG   960
TGTCCAGTCA GGGACGCCCA TCACCAATGA TCTCTTCAGC CAAGCCCTAC AGCATGCCCT  1020
TCAGGCCTCT GGGCAGCCCA GCCTTGCAGA CCAGTGGCAG CCCCAGCTGC AGCAGCTACG  1080
TGACATGGGC ATCCAGGACG ATGAGCTGAG CCTGCAGGCCAC TGCTGGGAC CGGTGGGGAC  1140
ATCCAAGCAG CCCTGGAGCT CATCTTTGCT GGAGGAGCCC TGCTTCCCC CTGCTTCCCC  1200
TGAACCCCCA GCAAGTTGCA GAGGCTACTG CCCTTGGGAG CATGAACTCC CATGACTCATGA  1260
ATCTCTCCCT GTC                                                     1273
```

```
MSLSDWHLAV KLADQPLTPK SILRLPETEL GEYSLGGYSI SFLKQLIAGK LQESVPDPEL   60
IDLIYCGRKL RDDQTLDFYG IQPGSTVHVL RKSWPEPDQK PEPVDKVAAM REFRVLHTAL  120
HSSSSYREAV FKMLSNKESL DQIIVATPGL SSDPIALGVL QDKDLFSVFA DPNMLDTLVP  180
AHPALVNAIV LVLHSVAGSA PMPGTDSSSR SMPSSSYRDM PGGFLFEGLS DDEDDFHPNT  240
RSTPSSSTPS SRPASLGYSG AAGPRPITQS ELATALALAS TPESSSHTPT PGTQGHSSGT  300
SPMSSGVQSG TPITNDLFSQ ALQHALQASG QPSLQSQWQP QLQQLRDMGI QDDELSLRPC  360
RPPVGTSKQP WSSSLLEEPH ELPASPEPPA SCRGYCPWEA LMKVPPSLP             409
```

FIG. 7

PLATELET ACTIVATION PROTEIN

CROSS REFERENCE TO RELATED APPLICATIONS

This application claims priority from U.S. Ser. No. 60/005,074, filed Oct. 6, 1995.

STATEMENT AS TO FEDERALLY SPONSORED RESEARCH

This invention was made with Government support under grant number HL-02348 awarded by the National Institutes of Health.

BACKGROUND OF THE INVENTION

The invention relates to platelet activation proteins.

The normal hemostatic system regulates bleeding and thrombosis through a series of complex interactions between components of the blood vessel wall, circulating blood platelets, and plasma proteins.

Because vascular injury causes a rapid loss of the protein, fluid, and cellular components of the blood, animals have developed rapid responses to patch the vessel and initiate its repair. These rapid responses are initiated by the platelet, a highly specialized cell that reacts to vascular injury. Normally, platelets circulate in the blood as quiescent and nonadherent cells, monitoring the integrity of the blood vessel. In response to vascular injury, platelets adhere to de-endothelialized areas and activate. Platelet activation induces profound morphologic and functional changes in the cell. Platelets change shape, aggregate with other platelets, and adhere to other cells. With full activation, platelets secrete the contents of their lysosomal, alpha, and dense granules, thereby expressing adhesion molecules, growth factors, coagulation enzymes, and other specialized molecules. Molecules expressed by activated platelets execute many of the complex cellular and biochemical processes that staunch the loss of blood and begin the process of vascular repair.

The cellular and biochemical processes initiated by platelets in response to vascular injury can be lifesaving, but in the absence of such injury these same processes can be deleterious. For example, unregulated arterial platelet thrombosis can occlude the blood supply to organs and lead to strokes, heart attacks, and limb necrosis.

SUMMARY OF THE INVENTION

A novel polypeptide, designated activated platelet protein-2 (APP-2), which is preferentially expressed on activated human platelets but not resting platelets, has now been discovered.

The invention includes a substantially pure DNA encoding a platelet activation polypeptide having a molecular weight of approximately 25 kilodaltons (kDa). Under non-reducing conditions, it can be naturally found in covalent association with two other proteins in a 145 kDa complex. The 25 kDa polypeptide as expressed in human platelets contains at least 2 putative phosphorylation sites. The protein of the invention can be characterized as containing an epitope which binds to the monoclonal antibody (MAb) 3B2.

Preferably, the encoded polypeptide is human APP-2, which includes at least 95% of the amino acid sequence of SEQ ID NO:4 (e.g. the protein encoded by SEQ ID NO:1). A preferred example of such a DNA would contain the nucleotide sequence of SEQ ID NO:3 or any degenerate variant of SEQ ID NO:3.

Most preferably, the DNA includes the nucleotide sequence of SEQ ID NO:1, or any degenerate variant of SEQ ID NO:1.

A substantially pure DNA containing a strand of at least 12 nucleotides, e.g., a hybridization probe of at least 20 nucleotides, 50 nucleotides, 100 nucleotides or more, which hybridizes at high stringency to a DNA having the sequence of SEQ ID NO:3, or the complement thereof, is also within the invention. Expression of APP-2 in a cell can be detected by (a) contacting mRNA obtained from the cell with a labeled hybridization probe comprising, for example, a single-stranded segment of isolated DNA encoding a fragment of APP-2; and (b) detecting hybridization of the probe with the MRNA.

By "high stringency" is meant the following DNA hybridization and wash conditions: hybridization at 42° C. in the presence of 50% formamide; a first wash at 65° C. with 2×SSC containing 1% SDS; followed by a second wash at 65° C. with 0.1×SSC.

By "substantially pure DNA" is meant DNA that is free of the genes which, in the naturally-occurring genome of the organism from which the DNA of the invention is derived, flank the DNA sequence of interest. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or CDNA fragment produced by polymerase chain reaction (PCR) or restriction endonuclease digestion) independent of other sequences. It also includes a recombinant DNA which (a) is part of a hybrid gene encoding additional polypeptide sequence, e.g., a fusion protein, or (b) has a sequence that is not a naturally-occurring nucleotide sequence (e.g., a degenerate variant of a natural sequence, or a sequence containing mutations which do not occur naturally). Also included is a recombinant which includes a portion of SEQ ID NO:3 and which encodes an alternative splice variant of APP-2, e.g., a polypeptide, the amino terminus of which differs from the amino terminus of SEQ ID NO:4.

The DNA should have at least about 50% identity to the coding sequence of SEQ ID NO:1 or 3, and preferably at least 70% (e.g., 80%, 90% or 95%). The identity between two nucleic acid or polypeptide sequences is a direct function of the number of matching or identical positions. For example, when a subunit position in both of the two sequences is occupied by the same monomeric subunit, e.g., if a position in each of two DNA molecules is occupied by an adenine, then they are identical at that position. For example, if half, e.g., 5 positions in a sequence 10 nucleotides in length, are identical, then the sequences have 50% sequence identity. The length of comparison sequences will generally be at least 50 nucleotides, preferably at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705). For purposes of calculating % sequence identity, gaps are considered to be mismatches.

The invention also includes a vector containing a DNA encoding a polypeptide which includes the amino acid sequence of SEQ ID NO:4, e.g., a construct in which the coding sequence is operably linked to a promoter or other regulatory sequences for expression of the polypeptide, and a cell containing such a vector. The cell may be procaryotic or eukaryotic (e.g., a mammalian cell such as a human cell) and preferably expresses the recombinant polypeptide encoded by SEQ ID NO:3.

The invention also includes a substantially pure platelet activation polypeptide as described above. By "platelet activation polypeptide" is meant a polypeptide having the amino acid sequence of a protein that is naturally preferentially expressed by activated platelets compared to resting platelets of an animal. Preferably, the animal is a vertebrate, e.g. a mammal such as a primate, including a human; alternatively the mammal is a rat, mouse, rabbit, guinea pig, hamster, cow, pig, horse, goat, sheep, dog, or cat.

Preferably, the polypeptide contains the amino acid sequence of human APP-2 (SEQ ID NO:4), e.g., in the form of a Flag-APP-2 fusion protein. By "polypeptide" is meant any chain of amino acids, regardless of length or post-translational modification (e.g., glycosylation or phosphorylation). The amino acid sequence of the polypeptide differs solely from SEQ ID NO:4 by conservative amino acid substitutions, e.g., substitution of one amino acid for another of the same class (e.g., valine for glycine, arginine for lysine, etc.) or by one or more non-conservative substitutions, deletions, or insertions located at positions of the amino acid sequence which do not destroy the function of the protein (e.g., its binding to Mab 3B2 or its covalent association in the 145 kDa complex). Preferably, the amino acid sequence of the platelet activation polypeptide is at least 50%, more preferably 70%, even more preferably 85% or 90%, and most preferably 95% identical to SEQ ID NO:4.

By a "substantially pure polypeptide" is meant a polypeptide which has been separated from components which naturally accompany it. Typically, the polypeptide is substantially pure when it is at least 60%, by weight, free from the proteins and other naturally-occurring organic molecules with which it is naturally associated. Preferably, the purity of the preparation is at least 75%, more preferably at least 90%, and most preferably at least 99%, by weight. A substantially pure APP-2 polypeptide may be obtained, for example, by extraction from a natural source (e.g., mammalian platelets); by expression of a recombinant nucleic acid encoding an APP-2 polypeptide; in cells or in a cell-free system; or by chemically synthesizing the protein. Purity can be measured by any appropriate method, e.g., column chromatography such as immunoaffinity chromatography using Mab 3B2, polyacrylamide gel electrophoresis, or HPLC analysis.

A protein is substantially free of naturally associated components when it is separated from those contaminants which accompany it in its natural state. Thus, a protein which is either chemically synthesized or produced in a cellular system different from the cell from which it naturally originates will be substantially free from its naturally associated components. Accordingly, substantially pure polypeptides include those derived from eukaryotic organisms but synthesized in E. coli or other prokaryotes.

In addition to substantially full-length polypeptides, the invention also includes fragments of these polypeptides. As used herein, "fragment," as applied to a polypeptide, will ordinarily be at least 10 residues, more typically at least 20 residues, and preferably at least 60 residues in length. Fragments of the APP-2 polypeptide can be generated by methods known to those skilled in the art. The ability of a candidate fragment to exhibit a characteristic of APP-2 (e.g., binding to Mab 3B2 or any other anti-APP-2 antibody) can be assessed by those methods described herein. Also included in the invention are APP-2 polypeptides which are encoded by portions of SEQ ID NO:3, e.g., products of alternative mRNA splicing or alternative protein processing events, or in which a section of APP-2 sequence, such as the transmembrane domain and/or intracellular domain, has been deleted. The sequence of the transmembrane domain is routinely determined by identifying a segment consisting of-predominantly hydrophobic residues characteristic of a transmembrane domain.

The invention also includes a polypeptide which includes at least 20 amino acids of APP-2. Preferably, the polypeptide includes at least 50, more preferably at least 100, more preferably at least 200, and most preferably at least 300 amino acids of APP-2. Preferably, the polypeptide is an antigenic fragment of APP-2 or a soluble fragment of APP-2 which lacks the transmembrane domain of APP-2.

APP-2 has been found in covalent association with a complex (APCOM) that migrates at an apparent molecular weight of 145 kDa under non-reducing conditions. This complex contains at least two proteins in addition to APP-2: one of approximately 45 kD and one of approximately 15 kD. These proteins and the APCOM are all within the invention. By virtue of its characteristic association with activated platelets, as opposed to unactivated platelets, the APCOM and its constituent proteins can be used to generate antibodies (such as MAb 3B2) diagnostic for activated platelets and for thrombus.

The invention also includes a polyclonal or monoclonal antibody which specifically binds to the platelet activation polypeptide of the invention. Preferably, the antibody is MAb 3B2 or binds to the same epitope as MAb 3B2. The invention encompasses not only an intact monoclonal antibody, but also an immunologically-active antibody fragment, e.g., a Fab or (Fab)$_2$ fragment; an engineered single chain Fv molecule; or a chimeric molecule, e.g., an antibody which contains the binding specificity of one antibody, e.g., of murine origin, and the remaining portions of another antibody, e.g., of human origin. In preferred embodiments, the antibody may be linked to a detectable label, e.g. a radioactive label, fluorescent label, paramagnetic label, or calorimetric label.

Also within the invention is a method of detecting an activated platelet in a biological sample, which includes the steps of contacting the sample with the labelled antibody, e.g., radioactively tagged MAb 3B2, and determining whether the antibody binds to a component of the sample. Antibody binding indicates that the sample contains an APP-2 polypeptide, and consequently, an activated platelet.

The labelled antibody may also be used diagnostically. For example, one can localize a platelet thrombus in an animal, e.g., a human patient suspected of having undesirable blood clots, by administering to the animal the labelled antibody, e.g., MAb 3B2, and determining where in the animal the label localizes. Detection of the label at a given site in the animal indicates the existence of a platelet thrombus at that site.

The antibody of the invention may also be used therapeutically, e.g., in a method of targeting a compound to an activated platelet in an animal, which includes the steps of administering to an animal a composition containing the compound linked to an anti-APP-2 antibody, e.g., MAb 3B2. Preferably, the compound is a thrombolytic agent such as urokinase, prourokinase, streptokinase, tissue-type plasminogen activator, staphylokinase, or vampire bat tissue plasminogen activator, to dissolve thrombi; an anti-thrombotic agent such as heparin, hirudin, or inhibitors of Factor Xa or Factor 5a, to inhibit thrombi formation; an anti-proliferative agent such as inhibitors of platelet-derived growth factor or heparin binding growth factor to inhibit cell proliferation, e.g., smooth muscle cell proliferation, at a thrombus site; or an anti-migration agent such as inhibitors of smooth muscle cell migration, e.g, an antibody or other specific inhibitor of urokinase or integrin function, to prevent or inhibit migration of cells which contribute to the obstruction of a blood vessel at a thrombus site.

The therapeutic agents may be linked to an anti-APP-2 MAb, e.g., MAb 3B2, using a covalent bond, such as a disulfide bond or a covalent crosslinking agent. The MAb and therapeutic agent may also be produced recombinantly, with the two components of the compound joined by a peptide bond.

Other features and advantages of the invention will be apparent from the following detailed description, and from the claims.

BRIEF DESCRIPTION OF THE DRAWINGS

FIG. 4 is a representation of the nucleotide sequence of SEQ ID NO:1.

FIG. 5 is a representation of the amino acid sequence of SEQ ID NO:2.

FIG. 6 is a representation of the nucleotide sequence of SEQ ID NO:3.

FIG. 7 is a representation of the amino acid sequence of SEQ ID NO:4. Underline indicates phosphorylation sites.

DETAILED DESCRIPTION

Characterization of APP-2

Figures 1A, 1B:
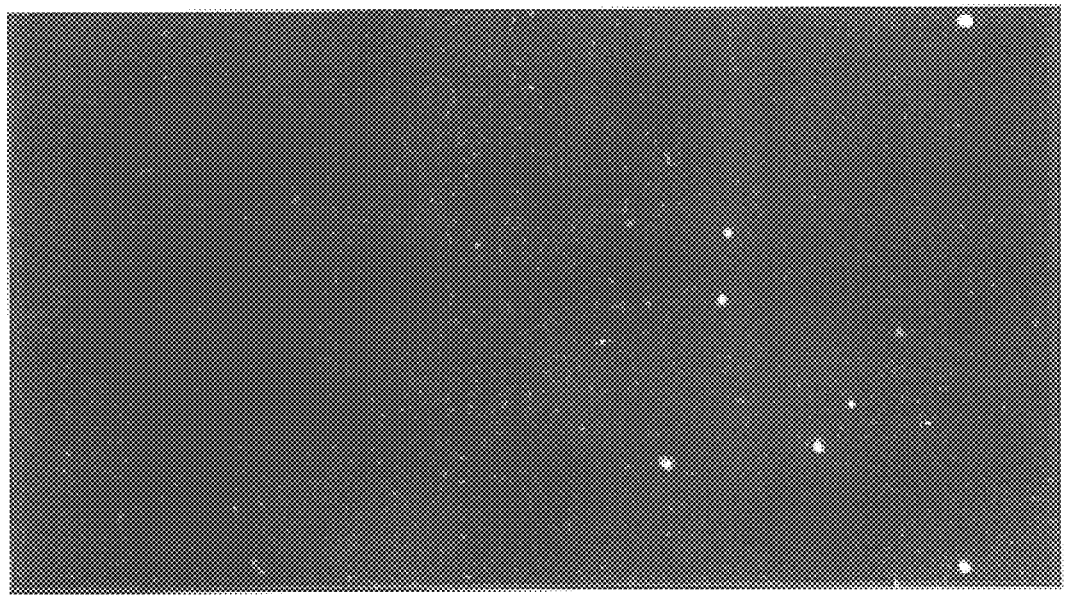
FIG. 1a is a photomicrograph showing the results of an immunofluorescent labelling experiment in which activated platelets were incubated with a control antibody, anti-digoxin.
FIG. 1b is a photomicrograph showing the results of an immunofluorescent labelling experiment in which activated platelets were incubated with MAb 3B2.

APP-2 was initially identified and isolated using 2-dimensional gel electrofocussing. APP-2 migrates to an apparent molecular weight of 145 and 25 kDa under non-reduced and reduced conditions, respectively. APP-2 can be detected on the surface of activated platelets by virtue of its binding to MAb 3B2. Platelet binding studies showed that anti-APP-2 binds preferentially to activated platelets and that this binding is saturable. Scatchard analysis indicates a single class of binding site with a binding constant of 4.19 nM and the presence of approximately 5000 binding sites per platelet. Studies of the association of APP-2 with the platelet membrane suggest that APP-2 is an integral membrane protein. Cloning of APP-2 revealed that APP-2 is a novel protein as its sequence shares homology with no known reported protein sequence.

The following experimental procedures were used to clone and characterize human APP-2.

Platelet Preparation and Biotinylation

Outdated units of platelet-rich human plasma were collected from blood banks. Platelets were isolated by differential centrifugation and then washed twice using a solution of 1 mM EDTA in Buffer A (3 mM Hepes, 5.5 M Glucose, 137 mM NaCl, 2.7 mM KCl, 3 mM $NaH_2PO_4$). The platelets were split into two different portions and counted. The portion to be activated was washed in Buffer A and resuspended to a concentration of $10^{10}$ cells/ml in Buffer B (Buffer A with 2 mM $CaCl_2$ and 1 MM $MgCl_2$). Platelets were activated by adding bovine thrombin (2 U/ml, Parke-Davis, Morris Plains, N.J.) and left to incubate at 37° C. for 30 min. The second (resting) portion of platelets was incubated in parallel in the absence of bovine thrombin. After centrifugation (2500 rpm, 20 min.) the supernatant was collected and frozen at −80° C. The platelet pellet was washed twice in Buffer A. After washing, the platelets were resuspended in Buffer A. For labelling, fresh NHS-LC-Biotin (Pierce, Ill.; 40 mg/ml) was added to platelets (resting or activated) at a concentration of 10 μg/ml of resuspended platelets and left to rotate for 2 h at 21° C. Following labelling, platelets were centrifuged, washed twice in Buffer A, resuspended in 20 ml Buffer A and stored at −80° C.

Preparative Two-Dimensional (2-D) Gel Electrophoresis

For 2-D electrophoresis, biotinylated resting or activated platelets (prepared from 20 Units of outdated plasma as described above) were diluted in sample buffer (0.125 M Tris Base, 20% glycerol, 2% sodium dodecyl sulfate (SDS)) at a concentration of 1:1 (v/v), boiled for 5 min., and centrifuged (3000 rpm, 30 min.). The proteins in the supernatant were precipitated with acetone (1:4 v/v) at 21° C. for 10 min. and centrifuged (14,000 rpm, 20 min.). The pellet was then resuspended in 10 ml electrofocussing buffer [9.9 M urea, 4% NP-40, 2.2% ampholytes (BIO-RAD Laboratories, Hercules, Calif.; pH 3–10), 100 mM dithiothreitol]. Preparative isoelectrofocussing was performed in a ROTOFOR® isoelectric focusing apparatus (BIO-RAD Laboratories). Prefocussing was performed with 45 ml of electrofocussing buffer for 1 h at 6 W. The sample was added and electrofocussing was performed for 4 h at 12 W. Fractions were collected into 65×12 mm plastic test tubes. The pH in each tube was measured to determine the pH gradient generated during the experiment and to facilitate the comparison of fractions from resting and activated platelets. Under the conditions described, isoelectrofocussing reproducibly created a pH gradient from 3–10. The isoelectric fractions with similar pH from resting and activated platelets were acetone-precipitated and separated on 12% SDS-polyacrylamide gels. The proteins were electroblotted to polyvinylidene difluoride membranes (PVDF) (Millipore, Bedford, Mass.) and blocked with 5% nonfat dry milk for 1 h. Biotinylated proteins were detected by incubating with streptavidin-alkaline phosphatase (Pierce, Rockford, Ill.; 1 μg/ml) diluted in 0.1% BSA in alkaline phosphatase buffer (0.1 M NaCl, 0.1 M Tris Base, 0.005 M $MgCl_2$, pH 9.5) for 30 min. After washing the membranes three times in 0.1% Tween-20 (Sigma, St. Louis, Mo.) in alkaline phosphatase buffer, the blots were developed with nitro-blue tetrazolium (330 μg/ml) and 5-bromo-4-chloro-3-indolyl phosphate (165 μg/ml) in alkaline phosphatase buffer. The blots from resting and activated platelets were compared to identify protein bands uniquely expressed by activated platelets. After identification of a protein band of interest, samples were separated in duplicate by SDS-PAGE.

A portion of the gel with one set of samples was stained with a reversible negative stain (Diversified Biotech, Mass.) while biotin detection was performed on the duplicate set of samples as described. Negatively stained bands matching the biotinylated protein bands were cut from the gel and electroeluted (25 mM Tris Base, 192 mM glycine, 0.1% SDS) overnight at 4° C., 10 mAmp/tube. Electroeluted proteins were acetone-precipitated and resuspended in phosphate-buffered saline (PBS). The concentration of the protein sample was determined by Coomassie Blue staining and silver staining.

Monoclonal Antibody Production and Purification

Female Balb/C mice (Charles River, Mass.) were immunized subcutaneously with the purified electroeluted proteins. When titers of immunized mice were detectable at a dilution higher than 1/1250, the splenocytes of one mouse were fused with a standard fusion partner cell line, e.g., sp2/0 myeloma cell line, to generate hybridoma cells using methods known in the art. Hybridoma cells were then tested for their production of antibody to activated platelets by radioimmunoassay. Culture media supernatants (25 µl) were incubated with $10^7$ thrombin-activated platelets in 100 µl buffer A and left to incubate at 21° C. for 1 h. Platelets were washed with 2 ml of cold buffer A, followed by centrifugation at 3000 rpm for 15 min. Then $^{125}$I goat anti-mouse antibody (50,000 cpm) was added to each platelet pellet and incubated for 1 h at 21° C. The platelets were again washed, centrifuged and the supernatant was removed. The platelet pellets were counted in gamma-counter. Selected hybridomas were cloned by limiting dilution. The isotype of the monoclonal antibody was determined using commercially available reagents (Zymed, Calif.). The hybridoma cells, e.g., those producing MAb 3B2, were expanded and inoculated into mice to generate ascites fluid. MAbs were purified from ascites fluid using known methods.

Purified APP-2 polypeptides (including antigenic fragments of APP-2) can be used as antigens to produce other MAbs capable of distinguishing activated platelets from resting platelets. To identify MAbs that bind to the same or similar epitope as MAb 3B2, purified APP-2 polypeptide (or activated platelets) is incubated either simultaneously or sequentially with a test MAb, e.g., a hybridoma tissue culture supernatant or ascites fluid of a MAb of undetermined specificity, and MAb 3B2 which is labelled with a detectable marker. Binding of MAb 3B2 to the activated platelets or purified APP-2 is then measured. A decrease in 3B2 antibody binding in the presence of the test antibody would indicate that the test antibody competes for the same or similar binding epitope on APP-2 as 3B2.

Radiolabelling of Antibody

Purified MAb 3B2 was radioiodinated to a specific activity of about 15,000 cpm/ng of antibody.

Immunofluorescence

Platelets were obtained from citrated blood by gel filtration using a SEPHAROSE® 2B agarose bead column. Platelets were diluted in Buffer B, and $10^7$ platelets were added to glass microscope slide chambers (Nunc, Naperville, Ill.; 8 wells/slide). The cells were allowed to absorb for 2 h at 21° C. Wells were washed three times in PBS, fixed 5 min. in formaldehyde, and then washed 4 times in PBS. Primary antibodies (at a concentration of 1 µg/ml in PBS with 1% BSA) were incubated for 90 min. at 21° C. The wells were washed three times in PBS. After a 1 h incubation at 37° C. with secondary antibody (goat anti-mouse FITC 1:500, Boehringer, Germany), wells were washed three more times with PBS and the slides were mounted with antifade solution (90% glycerol, 10% PBS, 1,4-diazobicyclo[2,2,2]octane (25 g/l)). The slides were examined at 200×magnification with a Nikon inverted microscope equipped with a mounted camera.

Immunodetection of APP-2 in Human Thrombus

Human aortic thrombus was fixed in paraformaldehyde and embedded in paraffin. Serial paraffin sections were probed with a control (anti-digoxin) MAb, an anti-P-selectin MAb, or MAb 3B2. Bound MAb was detected by goat antimouse antibody coupled to peroxidase. After development, the sections were visualized by light microscopy.

Detection of Platelet Activation

The monoclonal antibodies of the invention permit reliable and precise detection of platelet activation. To detect platelet activation in a biological sample, such as patient blood, the sample is incubated with a platelet activation specific antibody, e.g., MAb 3B2. Unbound antibody is washed away and bound antibody is detected using any standard label or method of labelling of antibodies known in the art, e.g., enzymes, radioisotopes, fluorescent compounds and metal chelates. For example, the antibodies of the invention can be used in an enzyme-linked immunosorbent assay (ELISA).

Binding of Monoclonal Antibodies to Platelets: Comparative Binding Assays

Platelets were isolated from citrated rabbit blood and gel filtered as described above. Platelets (90 µl, $10^7$ cells) were distributed to 65×12 mm plastic tubes. One portion of the platelets was activated with thrombin (10 µl, 1.5 U/ml) and left to incubate at 37° C. for 10 min. Another portion (resting) of platelets were incubated in parallel in the absence of thrombin. Platelets were fixed in 0.4% freshly prepared formaldehyde in phosphate buffer (pH 7.2, 10 µl) for 30 min. After the addition of 10 µl of neutralizing solution (20 mM $NH_4Cl$, 0.15 M NaCl, 0.3 M Tris Base, pH 7.2), platelets were washed in 2 ml Buffer A. Following centrifugation (3000 rpm, 10 min.) and removal of supernatant, platelets were incubated for 30 min. with $^{125}$I-labeled anti-APP-2 antibody (100,000 cpm/tube). After washing, the bound antibodies were recovered in the pellet following centrifugation (3000 rpm, 10 min.). Pellets were then counted in a gamma-counter.

Saturation Binding Assays

Platelets were isolated from fresh human blood by gel filtration. Platelets were diluted to $2.5 \times 10^7$ ml in Buffer B, and 50 µl was added to each tube. The cells were activated with 50 µl of thrombin (0.3 U/ml) in buffer B for 15 min. at 37° C. Increasing amounts of radiolabeled antibody (50 µl, 6260–1,400,000 cpm) were then added to each tube in duplicate in the presence or absence of unlabelled antibody (0.5 µg) as an inhibitor. After incubation at 21° C. for 45 min., cold Buffer A (2 ml) was added to each tube and the tubes were centrifuged for 15 min. at 3700 rpm. After removal of the supernatant, the platelet bound radioactivity was counted in a gamma-counter.

Immunoblotting

Platelets, smooth muscle cells, CCRF-CEM lymphoblastic leukemia cells (ATCC CCL 119), DAMI megakaryoblastic cells (Greenberg et al., 1988, Blood 72:1968–1977), and red blood cells (between 1 and 5 µg) were resuspended in sample buffer and boiled for 5 min. (β-mercaptoethanol was added for reduced samples). Following SDS-PAGE, the proteins were electroblotted to PVDF membranes and blocked. The PVDF membranes were incubated with primary antibody for 90 min. at 21° C. or overnight at 4° C. The blots were washed with TBS and incubated with secondary antibody (goat anti-mouse alkaline phosphatase 1:2000 [KPL, Gaithersburg, Md.]) for 1 h. After washing three times in 0.1% Tween-20 in alkaline phosphatase buffer, the bound antibody was detected colorimetrically as described above.

Association of APP-2 with Platelet Membranes

Platelets in Platelet-Rich Plasma (PRP) ($4\times10^8$, 1 ml) were activated in the presence of 2 µM of the calcium ionophore, A23187 (Sigma), at 37° C. for 1 h. After centrifugation (2000 rpm, 20 min) platelets were resuspended and washed twice in 1 ml Buffer A. The platelets were resuspended in 80 µl of one of the following solutions: Buffer A; 2 mM EDTA in Buffer A; 1 M Urea; 1 M NaCl; 0.1 M glycine pH 2.8; 0.1 M glycine pH 11; or 0.1% Triton-X 100 in Buffer A. After incubation at 21° C. for 1 h, samples were centrifuged for 20 min. at 2000 rpm. Without dislodging the platelet pellet, 50 µl of supernatant were recovered, concentrated by acetone-precipitation, resuspended in sample buffer, and electrophoresed on 7.5% SDS gels. The presence of APP-2 or, as a control, CD63 in the eluant was determined by immunoblotting with anti-CD63 monoclonal antibody (1 µg/ml; Biodesign, Kennebunkport, Me.) and anti-APP-2.

Effects of Anti-APP-2 on Platelet Aggregation $10^8$ platelets in 450 µl Buffer A were added to an aggregometer cuvette containing a stir bar. MAb 3B2 (50 µl, final concentration of 5 or 50 µg/ml) was added to the cuvette and incubated for several minutes while recording changes in light scattering (aggregometer, Chrono-Log). Then 5 µl of A23187 (Sigma, 2 µM final concentration) were then added to the cuvette and the aggregation of platelets was measured using standard methods known in the art.

Phosphorylation Experiments

Freshly isolated, platelet-rich human plasma (~$3\times10^8$ cells/ml in 3.5 ml) was mixed with ~950 µCi of $H_3{}^{32}PO_4$ and incubated at 37° C. for 1 hr. Then the calcium ionophore A23187 was added (2 µM) for 15 min. at 37° C. The platelets were isolated by centrifugation at 3000 rpm for 10 min. at 4° C. and lysed quickly in 0.5% SDS, 50 mM Tris-HCl (pH 8.0), and 1 mM dithiothreitol, and boiled for 15 min. The lysate was diluted with radioimmunoassay buffer and microfuged at 13,000 rpm for 60 min. The supernatant was precleared by incubation with MAb 64C5 coupled to sepharose for 2 hours. The supernatant was then split in half and 1 ml was incubated with 200 µl of MAb 3B2 or MAb 64C5 coupled to sepharose for 90 min. at 4° C. The supernatant was removed and the MAb-sepharose was washed twice with cold RIPA buffer. After centrifugation, 150 µl of sample buffer with 5% β-mercaptoethanol was added and the beads were boiled for 5 min. The samples were loaded onto 12.5% SDS-polyacrylamide gels for electrophoresis. Human platelet lysate was loaded into another lane as a control. After electroblotting to polyvinylidene difluoride membranes, the platelet lysate was immunoblotted with MAb 3B2 and the immunoprecipitates were exposed in a phosphorimager (Molecular Devices, Sunnyvale, Calif.).

Molecular Cloning of APP-2

After infecting *E. coli* Y1090 cells, phage from a lambda gt11 human bone marrow (5' stretch plus, cDNA library, Clonetech, Palo Alto, Calif.) were grown until visible plaques formed at 42° C. on LB ampicillin plates. Dried nitrocellulose filters, presoaked in isopropylthio-β-galactosidase (IPTG; 10 mM), were overlaid on bacterial lawn and left at 37° C. for 3.5 h. Following several washes in TBS, the filters were blocked in 5% milk and left overnight to incubate with monoclonal antibody. Filters were then processed as described above for immunoblotting. A total of 980,000 phages were screened using this procedure. Phage expressing a protein recognized by the anti-APP-2 antibody were purified to homogeneity by several rounds of screening. DNA hybridization methods were used to isolate clones containing additional cDNA sequences using well known methods, e.g., Sambrook et al, 1989. The cDNA probes were labelled by random priming (Boehringer Mannheim, Indianapolis, Ind.) using established methods. Radiolabelled probe was added to prehybridized filters (2 h at 42° C.) and incubated overnight at 42° C. Filters were then rinsed in a series of washes at 37° C., 42° C., 48° C. and 65° C. in 2×SSC solution containing 0.1% SDS. Filters were then exposed to X-ray films at −80° C. Phage cDNA isolated either by antibody screening or cDNA hybridization was subcloned into pUC18 vector. Both strands of the cDNA clones were sequenced according to known methods using a combination of primers specific for the internal sequence of the cDNA. Sequences were analyzed with the aid of the MACVECTOR program (IBI, New Haven, Conn.) and the NCBI database (NIH, Md.).

Using reagents derived from APP-2 cDNA clones containing some or all of SEQ ID NO:2, the isolation of a full-length APP-2 cDNA from any vertebrate species is well within the skill of those skilled in the art of molecular biology. For example, radiolabelled cDNA probes made from known cDNA inserts can be used to identify and isolate from platelet cDNA libraries cDNAs that contain regions with sequence homology to these cDNAs. The screening of cDNA libraries with radiolabelled cDNA probes is routine in the art of molecular biology (see Sambrook et al., 1989, *Molecular Cloning: a Laboratory Manual*, second edition., Cold Spring Harbor Press, Cold Spring Harbor, N.Y). The cDNA can be isolated and subcloned into a plasmid vector, and the plasmid DNA purified by standard techniques. The cDNA insert is sequenced using the dideoxy chain termination method well known in the art (Sambrook et al, supra). Oligonucleotide primers corresponding to bordering vector regions as well as primers prepared from previously isolated cDNA clones can be employed to determine the sequence of the entire gene.

DNA containing a sequence that encodes part or all of the amino acid sequence of an activated platelet protein homologous to human APP-2 can then be recloned into an expression vector, e.g., the pFlag vector system described below, using a variety of methods known in the art. For example, a recombinant polypeptide can be expressed as a Flag-fusion protein produced in *E. coli*. Antibodies (or fragments thereof) which bind to an epitope of APP-2 can then be used to detect expression of APP-2 polypeptide in the cDNA clones.

Bacterial Expression of APP-2

The cDNA encoding APP-2 was cloned into the pFlag vector (IBI, New Haven, Conn.) and used to transform DH5α *E. coli* cells (Gibco, Grand Island, N.Y.). Clones were grown on selection medium (LB+ampicillin). Cultures were diluted 1/100 into fresh medium in sterile flasks and grown with agitation at 37° C. until the $A_{600}=0.5$. IPTG (0.3 mM) was added to the cell suspension to induce protein expression, and the cells were grown for another 2 h at 37° C. The cells were centrifuged at 3000 rpm for 30 min., and the pellets were resuspended in 1/10 volume sample buffer with 5% β-mercaptoethanol prior to analysis on an electrophoretic gel.

Deposit

Under the terms of the Budapest Treaty on the International Recognition of the Deposit of Microorganisms for the Purpose of Patent Procedure, hybridoma 3B2 and plasmid APP-2 (in the pFlag vector) were deposited with the American Type Culture Collection (ATCC) of 10801 University Boulevard, Manassas, Va. 20110-2209 USA, on Oct. 6, 1995. The two deposits have been given the ATCC designations CRL-11986 and 97314, respectively.

Applicant's assignee, President and Fellows of Harvard College, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. § 122. The deposited material will be maintained with all the care necessary to keep it viable and uncontaminated for a period of at least five years after the most recent request for the furnishing of a sample of the deposited plasmid, and in any case, for a period of at least thirty (30) years after the date of deposit or for the enforceable life of the patent, whichever period is longer. Applicant's assignee acknowledges its duty to replace the deposit should the depository be unable to furnish a sample when requested due to the condition of the deposit.

Identification of APP-2 by 2D-Techniques

Analytical 2-D gel electrophoresis revealed several differences in the platelet cell activation protein pattern between resting and activated platelets. Although analytical 2-D electrophoresis offers tremendous resolution, its limitation resides in the resolution of only µg quantities of protein. To overcome this limiting factor and preserve the resolution of the 2-D system, separation of platelet proteins was accomplished by preparative 2-D electrophoresis. This technique enables the isolation of enough of an antigen, e.g., APP-2, to produce antibodies against it. APP-2 was routinely purified from 20 units of platelets. This represents approximately 10,000 times the amount which was separated using an analytical 2-D system.

To identify proteins specifically expressed by activated platelets, the external membrane proteins of resting and activated platelets were radioiodinated and subjected to 2-D gel analysis. These studies revealed two major proteins which were expressed only by activated platelets. A similar approach was employed to identify these activated platelet proteins using a preparative 2-D gel electrophoreses method. Biotinylated surface proteins from resting and activated platelets were subjected to preparative isoelectrofocussing followed by SDS-PAGE, electroblotting and steptavidin-alkaline phosphatase detection.

Many biotinylated proteins of the same molecular mass can be identified in the isoelectric fractions from both resting and activated platelet fractions. In addition, a biotinylated protein of about 25 kDa was identified in activated platelets which was not present in the corresponding isoelectric fraction of resting platelets. This protein was named APP-2. Following electrofocussing, APP-2 was electroeluted and used as an antigen to produce MAbs. Following somatic cell fusion, 170 out of 1960 microtiter plate wells showed hybridoma growth. Of these, 11% produced antibodies that bound to activated platelets. Based on its apparent avidity, one anti-APP-2 antibody, MAb 3B2, was selected and cloned. The anti-APP-2 MAb was found to have an IgG1 kappa isotype.

Detection of APP-2 in Platelets and Other Cells

Immunoblotting experiments were performed to analyze platelet lysate proteins. Under reducing conditions, the anti-APP-2 MAb detected a protein that migrated with an apparent molecular mass of 25 kDa, corresponding to the mass of APP-2 as identified by two-dimensional techniques. Under nonreducing conditions, APP-2 migrated with an apparent molecular mass of 145 kDa. When purified from a Tx-100 platelet lysate by immunoaffinity chromatography with an anti-APP-2 antibody column, the molecular mass was also 145 kDa under non-reducing conditions.

The immunoblotting experiments suggested that APP-2 was linked via disulfide bonds to other peptides in an activated platelet protein complex (APCOM). To identify the other peptide members of the APCOM, APP-2 was purified by immunoaffinity chromatography and SDS-PAGE. The complex was then reduced and subjected to repeated SDS-PAGE, and component polypeptides were detected by silver staining. Analysis following reduction of the APCOM indicates it is composed of 3 different sized polypeptides of 45 kDa (APP-45), 25 kDa (APP-2) and 15 kDa (APP-15), respectively.

Immunoblotting studies were also performed with smooth muscle cells, red blood cells, and DAMI cells, a megakaryoblastic cell line. APP-2 was detected only in the lysates from platelets and from DAMI cells.

Expression of APP-2 by Activated Platelets

Immunofluorescence studies were performed with purified anti-APP-2 antibody to determine whether APP-2 (and, by extension, the APP-2-containing APCOM) was detectable on the surface of activated platelets. Compared to a control (anti-digoxin) monoclonal antibody of the same isotype, only anti-APP-2 showed specific binding to activated platelets (FIG. 1a and FIG. 1b).

Figure 2:
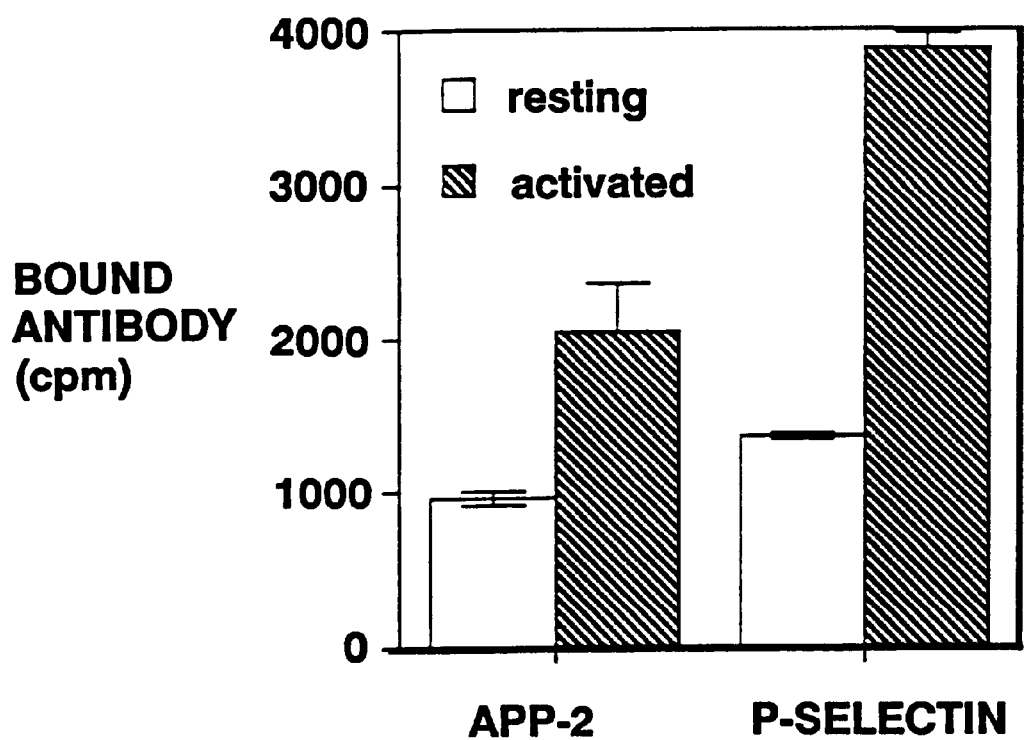
FIG. 2 is a bar graph showing a comparison of the expression of APP-2 before and after cell activation as detected by MAb 3B2 and expression of p-selectin (a platelet activation molecule selectively expressed on activated platelets) before and after cell activation as detected by an anti-p-selectin antibody.

Experiments were performed to determine whether APP-2 was preferentially expressed by resting or activated platelets. FIG. 2 shows a comparison of the expression of APP-2 and p-selectin (a platelet activation molecule selectively expressed on activated platelets) before and after cell activation, as detected by specific MAbs to each protein. Compared to the level of expression of p-selectin, there is minimal expression of APP-2 on resting platelets.

After cell activation, there is a significant increase in APP-2 expression compared to resting platelets. The expression of p-selectin also increased following cell activation. The magnitude of increase in binding of the anti-p-selectin MAb to activated platelets was significantly greater than that seen for the anti-APP-2 MAb, suggesting that there were more molecules of p-selectin expressed per activated platelet.

Saturation binding studies were performed with anti-APP-2 monoclonal antibody to determine the number of MAb 3B2 binding sites on activated platelets. The binding of anti-APP-2 to activated platelets was saturable and inhibited by an excess of unlabelled anti-APP-2 MAb. Analysis of the binding data indicated a single class of binding sites with 4683±784 molecules per activated platelet, representing about 40–50% of the number of p-selectin molecules per activated platelet. The anti-APP-2 antibody bound to platelets with a dissociation constant of 4.19 nN.

These data indicate that MAb 3B2 bound specifically and preferentially to activated platelets. Its binding was saturable and could be inhibited by competition with unlabelled antibody. Scatchard analysis indicated that there was only a single class of antigen with about 5000 molecules per platelet.

The Nature of APP-2's Association with the Platelet Membrane

Experiments were performed to determine if APP-2 was physically associated with the external surface of platelets as an integral or peripheral membrane protein. APP-2 was eluted from the platelet membrane by Triton X-100, but no significant amounts were removed by the following solutions: Buffer A; 2 mM EDTA; 1 M Urea; 1 M NaCl; 0.1 M glycine pH 2.8; or 0.1 M glycine pH 11. The elution profile was similar to the one obtained for CD63, which is an integral membrane protein. These results suggest that APP-2 (and, by extension, APCOM) is associated with the surface of platelets as an integral platelet membrane protein.

Effects of Anti-APP-2 MAb on Platelet Aggregation

The anti-APP-2 MAb was added to platelet-rich plasma before and after platelet stimulation with A23187. MAb 3B2 (at concentrations of 5 or 50 µg/ml) alone did not induce platelet aggregation. The anti-APP-2 MAb also had no apparent effect on the magnitude or rate of aggregation after platelets were stimulated with A23187. These data indicate that the addition of the MAb 3B2 to resting platelets did not induce aggregation of platelets and did not prevent them from aggregating following addition of platelet activation agent, A23187.

Molecular Cloning of the cDNA Coding for APP-2

To isolate a cDNA sequence coding for APP-2, a human bone marrow, lambda gt11 expression library was screened with anti-APP-2 MAb. Approximately 970,000 phages plaques were screened, and a positive clone was isolated. This clone was purified to homogeneity by repetitive subcloning. To confirm that the cDNA isolated encoded APP-2, it was ligated into the pFlag vector for expression in bacteria. Bacterial lysates containing the Flag-APP-2 fusion protein, or a negative control Flag-fusion protein, were analyzed by immunoblotting. The anti-APP-2 monoclonal antibody bound specifically to the induced Flag-APP-2 fusion protein, but not to the control Flag-fusion protein. Moreover, a control monoclonal antibody of the same isotype as the anti-APP-2 MAb did not bind to the Flag-APP-2 fusion protein. The Flag-APP-2 fusion protein had a molecular mass of 47 kDa under reduced conditions, which was consistent with the open reading frame predicted by DNA sequencing.

The APP-2 polypeptide can be enzymatically cleaved from the fusion protein using enterokinase (IBI, New Haven, Conn.). The cleavage products can then be subjected to further chromatography to purify the APP-2 polypeptide from the Flag portion of the fusion protein. For example, the Flag cleavage product can be removed from the mixture using commercially available reagents that bind to the Flag polypeptide (IBI, New Haven, Conn.). Alternatively, MAb 3B2 can be used to purify the APP-2 cleavage product from the mixture using immunoaffinity chromatography.

APP-2 Sequence Homologies and Motifs

Sequencing of isolated cDNA with specific internal primers in both directions gave several partial sequences which were aligned (Macvector™ Assemblign, IBI, New Haven, Conn.). The consensus sequence was analyzed against all the sequences reported to the NIH GENBANK® database. Although partial sequences showed homology with APP-2 sequence, no characterized sequence of a known reported gene matched the sequence of APP-2. Sequence analysis revealed that APP-2 is a novel protein: its amino acid sequence does not match any other reported protein sequence.

Full length DNA sequence encoding APP-2 was obtained by screening the same library with the isolated cDNA as a probe. Immunoblotting analysis confirmed that the recombinant polypeptide expressed the epitope recognized by MAb 3B2.

Phosphorylation of APP-2 in Activated Platelets

Immunoprecipitation studies were performed to determine if the potential phosphorylation sites on APP-2 were functional in activated platelets. In activated platelets incubated with $^{32}PO_4$ and activated, a 25 kDa band was specifically immunoprecipitated by the anti-APP antibody MAb 3B2, but not by a negative control (anti-fibrin) MAb. The band identified by MAb 3B2 comigrated with APP-2 as detected by immunoblotting in platelets in the same gel. Because the experimental conditions for this assay typically caused platelet activation, we were not able to determine whether APP-2 was phosphorylated in resting platelets under these conditions.

Immunodetection of APP-2 in Human Thrombus

Figure 3:
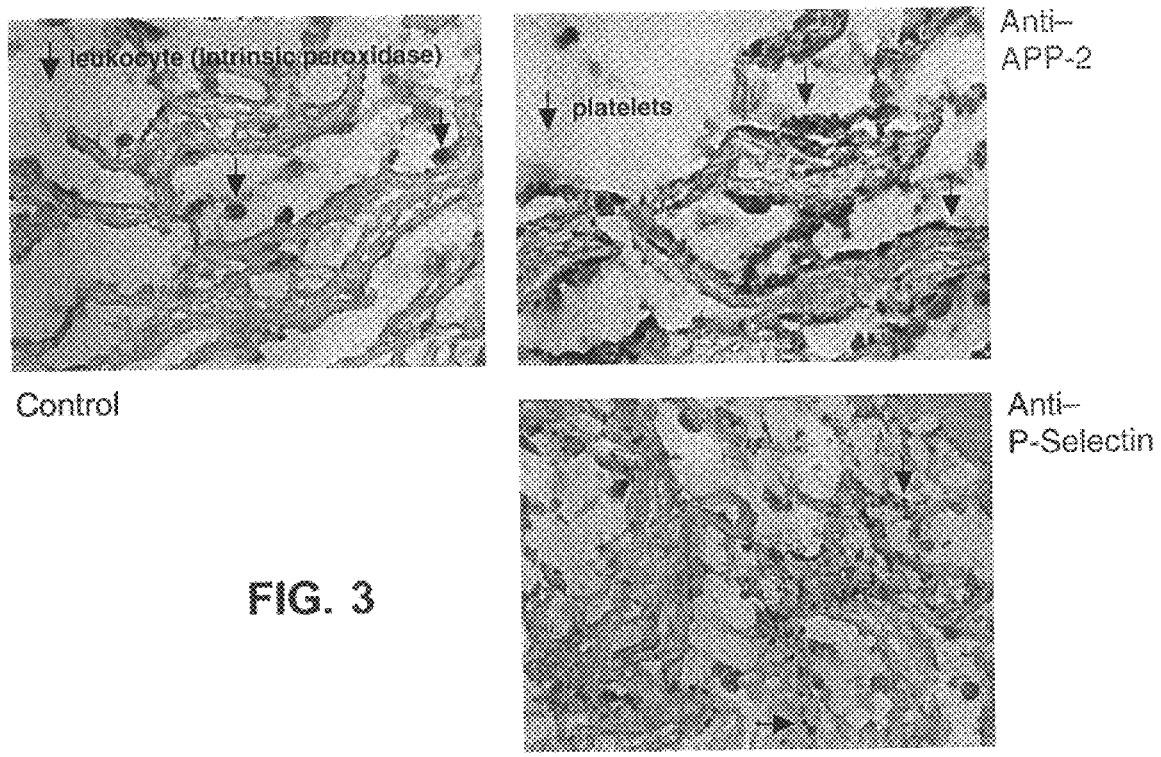
FIG. 3A–C are photomicrographs showing immunodetection of APP-2 in a human thrombus using MAb 3B2.

To determine if MAb 3B2 could specifically detect APP-2 in thrombus, serial sections of fixed aortic thrombus were probed with either MAb 3B2, an anti P-selectin MAb, or anti-digoxin MAb. FIG. 3A–C shows that MAb 3B2 and anti P-selectin both detect human thrombus, while the antdigoxin MAb does not. This suggests that the MAb 3B2 antibody, like P-selectin, can specifically recognize human thrombus.

Diagnostic and Therapeutic Uses

For administration to human patients, MAbs, e.g., MAb 3B2, can be humanized by methods known in the art, e.g, MAbs with a desired binding specificity can be commercially humanized (Scotgene, Scotland; Oxford Molecular, Palo Alto, Calif.). Monoclonal antibodies can be purified using known methods, such as absorption onto immobilized Protein A or immunoaffinity chromatography. Following purification, the MAbs of the invention or immunologically active fragments thereof, e.g., Fab, (Fab)$_2$, or Fv, can be administered to patients in a pharmaceutically acceptable excipient such as physiological saline. The MAbs and/or antibody-based compounds of the invention, e.g., MAbs linked to detectable labels or therapeutic agents, can be administered by any standard route including intraperitoneally, intramuscularly, subcutaneously, or intravenously. It is expected that the preferred route of administration will be intravenous. These compounds can be administered systemically to the bloodstream as well as locally within the blood vessel at the site of clot formation.

As is well known in the medical arts, dosages for any one patient depends on many factors, including the patients general health, sex, size, body surface area, age, as well as the particular compound to be administered, time and route of administration, and other drugs being administered concurrently. Dosages for compounds of the invention will vary, but a preferred dosage for intravenous administration is approximately 1 µg to 500 µg/ml/blood volume. Determination of correct dosage for a given application is well within the abilities of one of ordinary skill in the art of pharmacology.

The compounds of the invention, e.g., MAbs, or MAbs linked to other therapeutic agents such as antithrombotic agents, thrombolytic agents, anti-proliferative agents, or anti-migration agents, may also be administered simultaneously or sequentially with such agents. Preferred thrombolytic agents include plasminogen activators, e.g., urokinase, prourokinase, streptokinase, tissue-type plasminogen activator, staphylokinase or vampire bat tissue plasminogen activator, as well as physiologically active fragments thereof, e.g., single chain urokinase plasminogen activator (scu-PA) and hybrids. Thrombolytic agents are expected to be administered intravenously at approximately 0.1 to 2.0 mg per kg body weight. The optimal dosage may be adjusted according to the condition of the patient and response of the patient to therapy.

Other embodiments are within the following claims.

We claim:

1. A substantially pure DNA encoding a naturally-occurring platelet activation polypeptide, said polypeptide comprising a sequence at least 70% identical to the coding sequence of SEQ ID NO:1.

2. A substantially pure DNA encoding a human APP-2 polypeptide comprising an amino acid sequence identical to at least 95% of SEQ ID NO:4, wherein said polypeptide binds to monoclonal antibody (MAb) 3B2 (ATCC Designation CRL-11986).

3. A substantially pure DNA comprising the coding sequence of SEQ ID NO:3.

4. A substantially pure DNA comprising a strand of at least 20 nucleotides which hybridizes at high stringency to a DNA complementary to the coding sequence of SEQ ID NO:3.

5. A substantially pure DNA which hybridizes at high stringency to a DNA probe consisting of a sequence of 50 nucleotides complementary to the coding sequence of SEQ ID NO:3.

6. A vector comprising the DNA of claim 1.

7. The DNA of claim 1, wherein said DNA is operably linked to a regulatory sequence for expression of said polypeptide, said regulatory sequence comprising a promoter.

8. A cell comprising the DNA of claim 7.

9. A substantially pure DNA encoding a naturally-occurring platelet activation polypeptide, said DNA comprising the coding sequence of SEQ ID NO:1 or a degenerate variant thereof.

10. The DNA of claim 9, wherein said DNA comprises the coding sequence of SEQ ID NO:1.

11. A vector comprising the DNA of claim 9.

12. The DNA of claim 9, wherein said DNA is operably linked to a promoter.

13. A substantially pure DNA encoding a naturally-occurring platelet activation polypeptide, said DNA comprising coding sequence of SEQ ID NO:3 or a degenerate variant thereof.

14. The DNA of claim 13, wherein said DNA comprises the coding sequence of SEQ ID NO:3.

15. A vector comprising the DNA of claim 13.

16. The DNA of claim 13, wherein said DNA is operably linked to a promoter.

17. A substantially pure DNA encoding a polypeptide comprising the amino acid sequence of SEQ ID NO:4.

18. A substantially pure DNA encoding a naturally-occurring platelet activation polypeptide, wherein said DNA hybridizes at high stringency to a nucleic acid having a sequence complementary to the coding sequence of SEQ ID NO:1.

19. A substantially pure DNA encoding a naturally-occurring platelet activation polypeptide, wherein said DNA hybridizes at high stringency to a nucleic acid having a sequence complementary to the coding sequence of SEQ ID NO:3.

20. A substantially pure DNA encoding a naturally-occurring platelet activation polypeptide, wherein said DNA hybridizes at high stringency to a DNA probe consisting of a sequence of 50 nucleotides complementary to a 50-nucleotide portion of the coding sequence of SEQ ID NO:3.

21. A substantially pure DNA encoding a naturally-occurring platelet activation polypeptide, wherein said DNA hybridizes at high stringency to a DNA probe consisting of a sequence of 50 nucleotides complementary to a 50-nucleotide portion of the coding sequence of SEQ ID NO:1.

22. A substantially pure DNA comprising a strand which hybridizes at high stringency to a DNA complementary to the coding sequence of SEQ ID NO:3, wherein the length of said DNA consists of 20 to 100 nucleotides.

23. The DNA of claim 22, wherein the length of said DNA is 20 to 50 nucleotides, inclusive.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1373 base pairs
      (B) TYPE: nucleic acid
      (C) STRANDEDNESS: both
      (D) TOPOLOGY: linear (ii) MOLECULE TYPE: cDNA (ix) FEATURE:
      (A) NAME/KEY: Coding Sequence
      (B) LOCATION: 44...1321

(xi) SEQUENCE DESCRIPTION: SEQ ID NO:1:

```
GCGAGAGGGC CAGAGGAGAA AGAGAGAGCG CGAAAGAGAG AGG ATG TCT CTC TCA        55
                                             Met Ser Leu Ser
                                              1

GAC TGG CAC CTG GCG GTG AAG CTG GCT GAC CAG CCA CTT ACT CCA AAG       103
Asp Trp His Leu Ala Val Lys Leu Ala Asp Gln Pro Leu Thr Pro Lys
 5                  10                  15                  20

TCT ATT CTT CGG TTG CCA GAG ACA GAA CTG GGA GAA TAC TCG CTA GGG       151
Ser Ile Leu Arg Leu Pro Glu Thr Glu Leu Gly Glu Tyr Ser Leu Gly
                25                  30                  35

GGC TAT AGT ATT TCA TTT CTG AAG CAG CTT ATT GCT GGC AAA CTC CAG       199
Gly Tyr Ser Ile Ser Phe Leu Lys Gln Leu Ile Ala Gly Lys Leu Gln
            40                  45                  50

GAG TCT GTT CCA GAC CCT GAG CTG ATT GAT CTG ATC TAC TGT GGT CGG       247
Glu Ser Val Pro Asp Pro Glu Leu Ile Asp Leu Ile Tyr Cys Gly Arg
        55                  60                  65

AAG CTA AAA GAT GAC CAG ACA CTT GAC TTC TAT GGC ATT CAA CCT GGG       295
Lys Leu Lys Asp Asp Gln Thr Leu Asp Phe Tyr Gly Ile Gln Pro Gly
    70                  75                  80

TCC ACT GTC CAT GTT CTG CGA AAG TCC TGG CCT GAA CCT GAT CAG AAA       343
Ser Thr Val His Val Leu Arg Lys Ser Trp Pro Glu Pro Asp Gln Lys
85                  90                  95                 100

CCG GAA CCT GTG GAC AAA GTG GCT GCC ATG AGA GAG TTC CGG GTG TTG       391
Pro Glu Pro Val Asp Lys Val Ala Ala Met Arg Glu Phe Arg Val Leu
                105                 110                 115

CAC ACT GCC CTG CAC AGC AGC TCC TCT TAC AGG GAG GCG GTC TTT AAG       439
His Thr Ala Leu His Ser Ser Ser Ser Tyr Arg Glu Ala Val Phe Lys
            120                 125                 130

ATG CTC AGC AAT AAG GAG TCT CTG GAT CAG ATC ATT GTG GCC ACC CCA       487
Met Leu Ser Asn Lys Glu Ser Leu Asp Gln Ile Ile Val Ala Thr Pro
        135                 140                 145
```

-continued

```
GGC CTC AGC AGT GAC CCT ATT GCT CTT GGG GTT CTC CAG GAC AAG GAC         535
Gly Leu Ser Ser Asp Pro Ile Ala Leu Gly Val Leu Gln Asp Lys Asp
        150                 155                 160

CTC TTC TCT GTC TTC GCT GAT CCC AAT ATG CTT GAT ACG TTG GTG CCT         583
Leu Phe Ser Val Phe Ala Asp Pro Asn Met Leu Asp Thr Leu Val Pro
165                 170                 175                 180

GCT CAC CCA GCC CTC GTC AAT GCC ATT GTC CTG GTT CTG CAC TCC GTA         631
Ala His Pro Ala Leu Val Asn Ala Ile Val Leu Val Leu His Ser Val
                185                 190                 195

GCA GGC AGT GCC CCA ATG CCT GGG ACT GAC TCC TCT TCC CGG AGC ATG         679
Ala Gly Ser Ala Pro Met Pro Gly Thr Asp Ser Ser Ser Arg Ser Met
                    200                 205                 210

CCC TCC AGC TCA TAC CGG GAT ATG CCA GGT GGC TTC CTG TTT GAA GGG         727
Pro Ser Ser Ser Tyr Arg Asp Met Pro Gly Gly Phe Leu Phe Glu Gly
            215                 220                 225

CTC TCA GAT GAT GAG GAT GAC TTT CAC CCA AAC ACC AGG TCC ACA CCC         775
Leu Ser Asp Asp Glu Asp Asp Phe His Pro Asn Thr Arg Ser Thr Pro
        230                 235                 240

TCT AGC AGT ACT CCC AGC TCC CGC CCA GCC TCC CTG GGG TAC AGT GGA         823
Ser Ser Ser Thr Pro Ser Ser Arg Pro Ala Ser Leu Gly Tyr Ser Gly
245                 250                 255                 260

GCT GCT GGG CCC CGG CCC ATC ACC CAG AGT GAG CTG GCC ACC GCC TTG         871
Ala Ala Gly Pro Arg Pro Ile Thr Gln Ser Glu Leu Ala Thr Ala Leu
                265                 270                 275

GCC CTG GCC AGC ACT CCG GAG AGC AGC TCT CAC ACA CCG ACT CCT GGC         919
Ala Leu Ala Ser Thr Pro Glu Ser Ser Ser His Thr Pro Thr Pro Gly
                    280                 285                 290

ACC CAG GGT CAT TCC TCA GGG ACC TCA CCA ATG TCC TCT GGT GTC CAG         967
Thr Gln Gly His Ser Ser Gly Thr Ser Pro Met Ser Ser Gly Val Gln
            295                 300                 305

TCA GGG ACG CCC ATC ACC AAT GAT CTC TTC AGC CAA GCC CTA CAG CAT        1015
Ser Gly Thr Pro Ile Thr Asn Asp Leu Phe Ser Gln Ala Leu Gln His
        310                 315                 320

GCC CTT CAG GCC TCT GGG CAG CCC AGC CTT CAG AGC CAG TGG CAG CCC        1063
Ala Leu Gln Ala Ser Gly Gln Pro Ser Leu Gln Ser Gln Trp Gln Pro
325                 330                 335                 340

CAG CTG CAG CAG CTA CGT GAC ATG GGC ATC CAG GAC GAT GAG CTG AGC        1111
Gln Leu Gln Gln Leu Arg Asp Met Gly Ile Gln Asp Asp Glu Leu Ser
                345                 350                 355

CTG CGG CCC TGC AGG CCA CCG GTG GGG ACA TCC AAG CAG CCC TGG AGC        1159
Leu Arg Pro Cys Arg Pro Pro Val Gly Thr Ser Lys Gln Pro Trp Ser
                    360                 365                 370

TCA TCT TTG CTG GAG GAG CCC CAT GAA CTC CCT GCT TCC CCT GAA CCC        1207
Ser Ser Leu Leu Glu Glu Pro His Glu Leu Pro Ala Ser Pro Glu Pro
            375                 380                 385

CCA GCA AGT TGC AGA GGC TAC TGC CCT TGG GAG GCA CTC ATG AAG GTG        1255
Pro Ala Ser Cys Arg Gly Tyr Cys Pro Trp Glu Ala Leu Met Lys Val
        390                 395                 400

CCT CCA TCT CTC CCT TCC CCA ATA TAC CTG ATG GTC AAC TCT AAA AAA        1303
Pro Pro Ser Leu Pro Ser Pro Ile Tyr Leu Met Val Asn Ser Lys Lys
405                 410                 415                 420

AAA AAA AAA AAA AAA AAA TGAAATACCA CTACTCTGAT CGTTTTTTCA CTGACCCG      1359
Lys Lys Lys Lys Lys Lys
                425

GTGAGGCGGC GCGA                                                       1373
```

(2) INFORMATION FOR SEQ ID NO:2:

(i) SEQUENCE CHARACTERISTICS:

(A) LENGTH: 426 amino acids
       (B) TYPE: amino acid
       (D) TOPOLOGY: linear (ii) MOLECULE TYPE: protein (v) FRAGMENT TYPE: internal (xi) SEQUENCE DESCRIPTION: SEQ ID NO:2:

Met Ser Leu Ser Asp Trp His Leu Ala Val Lys Leu Ala Asp Gln Pro
 1               5                  10                  15

Leu Thr Pro Lys Ser Ile Leu Arg Leu Pro Glu Thr Glu Leu Gly Glu
            20                  25                  30

Tyr Ser Leu Gly Gly Tyr Ser Ile Ser Phe Leu Lys Gln Leu Ile Ala
        35                  40                  45

Gly Lys Leu Gln Glu Ser Val Pro Asp Pro Glu Leu Ile Asp Leu Ile
    50                  55                  60

Tyr Cys Gly Arg Lys Leu Lys Asp Asp Gln Thr Leu Asp Phe Tyr Gly
 65                  70                  75                  80

Ile Gln Pro Gly Ser Thr Val His Val Leu Arg Lys Ser Trp Pro Glu
                85                  90                  95

Pro Asp Gln Lys Pro Glu Pro Val Asp Lys Val Ala Ala Met Arg Glu
            100                 105                 110

Phe Arg Val Leu His Thr Ala Leu His Ser Ser Ser Tyr Arg Glu
        115                 120                 125

Ala Val Phe Lys Met Leu Ser Asn Lys Glu Ser Leu Asp Gln Ile Ile
    130                 135                 140

Val Ala Thr Pro Gly Leu Ser Ser Asp Pro Ile Ala Leu Gly Val Leu
145                 150                 155                 160

Gln Asp Lys Asp Leu Phe Ser Val Phe Ala Asp Pro Asn Met Leu Asp
                165                 170                 175

Thr Leu Val Pro Ala His Pro Ala Leu Val Asn Ala Ile Val Leu Val
            180                 185                 190

Leu His Ser Val Ala Gly Ser Ala Pro Met Pro Gly Thr Asp Ser Ser
    195                 200                 205

Ser Arg Ser Met Pro Ser Ser Ser Tyr Arg Asp Met Pro Gly Gly Phe
210                 215                 220

Leu Phe Glu Gly Leu Ser Asp Asp Glu Asp Asp Phe His Pro Asn Thr
225                 230                 235                 240

Arg Ser Thr Pro Ser Ser Ser Thr Pro Ser Ser Arg Pro Ala Ser Leu
                245                 250                 255

Gly Tyr Ser Gly Ala Ala Gly Pro Arg Pro Ile Thr Gln Ser Glu Leu
            260                 265                 270

Ala Thr Ala Leu Ala Leu Ala Ser Thr Pro Glu Ser Ser His Thr
    275                 280                 285

Pro Thr Pro Gly Thr Gln Gly His Ser Ser Gly Thr Ser Pro Met Ser
    290                 295                 300

Ser Gly Val Gln Ser Gly Thr Pro Ile Thr Asn Asp Leu Phe Ser Gln
305                 310                 315                 320

Ala Leu Gln His Ala Leu Gln Ala Ser Gly Gln Pro Ser Leu Gln Ser
                325                 330                 335

Gln Trp Gln Pro Gln Leu Gln Leu Arg Asp Met Gly Ile Gln Asp
            340                 345                 350

Asp Glu Leu Ser Leu Arg Pro Cys Arg Pro Val Gly Thr Ser Lys
        355                 360                 365

```
Gln Pro Trp Ser Ser Ser Leu Leu Glu Glu Pro His Glu Leu Pro Ala
    370                 375                 380

Ser Pro Glu Pro Pro Ala Ser Cys Arg Gly Tyr Cys Pro Trp Glu Ala
385                 390                 395                 400

Leu Met Lys Val Pro Pro Ser Leu Pro Ser Pro Ile Tyr Leu Met Val
                405                 410                 415

Asn Ser Lys Lys Lys Lys Lys Lys
        420                 425
```

(2) INFORMATION FOR SEQ ID NO:3:

(i) SEQUENCE CHARACTERISTICS:
        (A) LENGTH: 1273 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: Coding Sequence
        (B) LOCATION: 44...1273

(xi) SEQUENCE DESCRIPTION: SEQ ID NO:3:

```
GCGAGAGGGC CAGAGGAGAA AGAGAGAGCG CGAAAGAGAG AGG ATG TCT CTC TCA        55
                                              Met Ser Leu Ser
                                                1

GAC TGG CAC CTG GCG GTG AAG CTG GCT GAC CAG CCA CTT ACT CCA AAG      103
Asp Trp His Leu Ala Val Lys Leu Ala Asp Gln Pro Leu Thr Pro Lys
  5                  10                  15                  20

TCT ATT CTT CGG TTG CCA GAG ACA GAA CTG GGA GAA TAC TCG CTA GGG      151
Ser Ile Leu Arg Leu Pro Glu Thr Glu Leu Gly Glu Tyr Ser Leu Gly
                 25                  30                  35

GGC TAT AGT ATT TCA TTT CTG AAG CAG CTT ATT GCT GGC AAA CTC CAG      199
Gly Tyr Ser Ile Ser Phe Leu Lys Gln Leu Ile Ala Gly Lys Leu Gln
             40                  45                  50

GAG TCT GTT CCA GAC CCT GAG CTG ATT GAT CTG ATC TAC TGT GGT CGG      247
Glu Ser Val Pro Asp Pro Glu Leu Ile Asp Leu Ile Tyr Cys Gly Arg
         55                  60                  65

AAG CTA AAA GAT GAC CAG ACA CTT GAC TTC TAT GGC ATT CAA CCT GGG      295
Lys Leu Lys Asp Asp Gln Thr Leu Asp Phe Tyr Gly Ile Gln Pro Gly
 70                  75                  80

TCC ACT GTC CAT GTT CTG CGA AAG TCC TGG CCT GAA CCT GAT CAG AAA      343
Ser Thr Val His Val Leu Arg Lys Ser Trp Pro Glu Pro Asp Gln Lys
 85                  90                  95                 100

CCG GAA CCT GTG GAC AAA GTG GCT GCC ATG AGA GAG TTC CGG GTG TTG      391
Pro Glu Pro Val Asp Lys Val Ala Ala Met Arg Glu Phe Arg Val Leu
                105                 110                 115

CAC ACT GCC CTG CAC AGC AGC TCC TCT TAC AGG GAG GCG GTC TTT AAG      439
His Thr Ala Leu His Ser Ser Ser Ser Tyr Arg Glu Ala Val Phe Lys
            120                 125                 130

ATG CTC AGC AAT AAG GAG TCT CTG GAT CAG ATC ATT GTG GCC ACC CCA      487
Met Leu Ser Asn Lys Glu Ser Leu Asp Gln Ile Ile Val Ala Thr Pro
        135                 140                 145

GGC CTC AGC AGT GAC CCT ATT GCT CTT GGG GTT CTC CAG GAC AAG GAC      535
Gly Leu Ser Ser Asp Pro Ile Ala Leu Gly Val Leu Gln Asp Lys Asp
150                 155                 160

CTC TTC TCT GTC TTC GCT GAT CCC AAT ATG CTT GAT ACG TTG GTG CCT      583
Leu Phe Ser Val Phe Ala Asp Pro Asn Met Leu Asp Thr Leu Val Pro
165                 170                 175                 180

GCT CAC CCA GCC CTC GTC AAT GCC ATT GTC CTG GTT CTG CAC TCC GTA      631
Ala His Pro Ala Leu Val Asn Ala Ile Val Leu Val Leu His Ser Val
```

```
            185                 190                 195
GCA GGC AGT GCC CCA ATG CCT GGG ACT GAC TCC TCT TCC CGG AGC ATG        679
Ala Gly Ser Ala Pro Met Pro Gly Thr Asp Ser Ser Ser Arg Ser Met
            200                 205                 210

CCC TCC AGC TCA TAC CGG GAT ATG CCA GGT GGC TTC CTG TTT GAA GGG        727
Pro Ser Ser Ser Tyr Arg Asp Met Pro Gly Gly Phe Leu Phe Glu Gly
            215                 220                 225

CTC TCA GAT GAT GAG GAT GAC TTT CAC CCA AAC ACC AGG TCC ACA CCC        775
Leu Ser Asp Asp Glu Asp Asp Phe His Pro Asn Thr Arg Ser Thr Pro
            230                 235                 240

TCT AGC AGT ACT CCC AGC TCC CGC CCA GCC TCC CTG GGG TAC AGT GGA        823
Ser Ser Ser Thr Pro Ser Ser Arg Pro Ala Ser Leu Gly Tyr Ser Gly
245                 250                 255                 260

GCT GCT GGG CCC CGG CCC ATC ACC CAG AGT GAG CTG GCC ACC GCC TTG        871
Ala Ala Gly Pro Arg Pro Ile Thr Gln Ser Glu Leu Ala Thr Ala Leu
            265                 270                 275

GCC CTG GCC AGC ACT CCG GAG AGC AGC TCT CAC ACA CCG ACT CCT GGC        919
Ala Leu Ala Ser Thr Pro Glu Ser Ser Ser His Thr Pro Thr Pro Gly
            280                 285                 290

ACC CAG GGT CAT TCC TCA GGG ACC TCA CCA ATG TCC TCT GGT GTC CAG        967
Thr Gln Gly His Ser Ser Gly Thr Ser Pro Met Ser Ser Gly Val Gln
            295                 300                 305

TCA GGG ACG CCC ATC ACC AAT GAT CTC TTC AGC CAA GCC CTA CAG CAT       1015
Ser Gly Thr Pro Ile Thr Asn Asp Leu Phe Ser Gln Ala Leu Gln His
310                 315                 320

GCC CTT CAG GCC TCT GGG CAG CCC AGC CTT CAG AGC CAG TGG CAG CCC       1063
Ala Leu Gln Ala Ser Gly Gln Pro Ser Leu Gln Ser Gln Trp Gln Pro
325                 330                 335                 340

CAG CTG CAG CAG CTA CGT GAC ATG GGC ATC CAG GAC GAT GAG CTG AGC       1111
Gln Leu Gln Gln Leu Arg Asp Met Gly Ile Gln Asp Asp Glu Leu Ser
            345                 350                 355

CTG CGG CCC TGC AGG CCA CCG GTG GGG ACA TCC AAG CAG CCC TGG AGC       1159
Leu Arg Pro Cys Arg Pro Pro Val Gly Thr Ser Lys Gln Pro Trp Ser
            360                 365                 370

TCA TCT TTG CTG GAG GAG CCC CAT GAA CTC CCT GCT TCC CCT GAA CCC       1207
Ser Ser Leu Leu Glu Glu Pro His Glu Leu Pro Ala Ser Pro Glu Pro
            375                 380                 385

CCA GCA AGT TGC AGA GGC TAC TGC CCT TGG GAG GCA CTC ATG AAG GTG       1255
Pro Ala Ser Cys Arg Gly Tyr Cys Pro Trp Glu Ala Leu Met Lys Val
390                 395                 400

CCT CCA TCT CTC CCT GTC                                                1273
Pro Pro Ser Leu Pro Val
405                 410

(2) INFORMATION FOR SEQ ID NO:4:

(i) SEQUENCE CHARACTERISTICS:
        (A) LENGTH: 410 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:4:

Met Ser Leu Ser Asp Trp His Leu Ala Val Lys Leu Ala Asp Gln Pro
 1               5                  10                  15

Leu Thr Pro Lys Ser Ile Leu Arg Leu Pro Glu Thr Glu Leu Gly Glu
                20                  25                  30

Tyr Ser Leu Gly Gly Tyr Ser Ile Ser Phe Leu Lys Gln Leu Ile Ala
```

-continued

```
                    35                    40                    45
Gly Lys Leu Gln Glu Ser Val Pro Asp Pro Glu Leu Ile Asp Leu Ile
    50                  55                  60

Tyr Cys Gly Arg Lys Leu Lys Asp Asp Gln Thr Leu Asp Phe Tyr Gly
65                  70                  75                  80

Ile Gln Pro Gly Ser Thr Val His Val Leu Arg Lys Ser Trp Pro Glu
                85                  90                  95

Pro Asp Gln Lys Pro Glu Pro Val Asp Lys Val Ala Ala Met Arg Glu
            100                 105                 110

Phe Arg Val Leu His Thr Ala Leu His Ser Ser Ser Ser Tyr Arg Glu
        115                 120                 125

Ala Val Phe Lys Met Leu Ser Asn Lys Glu Ser Leu Asp Gln Ile Ile
    130                 135                 140

Val Ala Thr Pro Gly Leu Ser Ser Asp Pro Ile Ala Leu Gly Val Leu
145                 150                 155                 160

Gln Asp Lys Asp Leu Phe Ser Val Phe Ala Asp Pro Asn Met Leu Asp
                165                 170                 175

Thr Leu Val Pro Ala His Pro Ala Leu Val Asn Ala Ile Val Leu Val
            180                 185                 190

Leu His Ser Val Ala Gly Ser Ala Pro Met Pro Gly Thr Asp Ser Ser
        195                 200                 205

Ser Arg Ser Met Pro Ser Ser Ser Tyr Arg Asp Met Pro Gly Gly Phe
    210                 215                 220

Leu Phe Glu Gly Leu Ser Asp Asp Glu Asp Asp Phe His Pro Asn Thr
225                 230                 235                 240

Arg Ser Thr Pro Ser Ser Ser Thr Pro Ser Ser Arg Pro Ala Ser Leu
                245                 250                 255

Gly Tyr Ser Gly Ala Ala Gly Pro Arg Pro Ile Thr Gln Ser Glu Leu
            260                 265                 270

Ala Thr Ala Leu Ala Leu Ala Ser Thr Pro Glu Ser Ser Ser His Thr
        275                 280                 285

Pro Thr Pro Gly Thr Gln Gly His Ser Ser Gly Thr Ser Pro Met Ser
    290                 295                 300

Ser Gly Val Gln Ser Gly Thr Pro Ile Thr Asn Asp Leu Phe Ser Gln
305                 310                 315                 320

Ala Leu Gln His Ala Leu Gln Ala Ser Gly Gln Pro Ser Leu Gln Ser
                325                 330                 335

Gln Trp Gln Pro Gln Leu Gln Leu Arg Asp Met Gly Ile Gln Asp
            340                 345                 350

Asp Glu Leu Ser Leu Arg Pro Cys Arg Pro Pro Val Gly Thr Ser Lys
        355                 360                 365

Gln Pro Trp Ser Ser Ser Leu Leu Glu Glu Pro His Glu Leu Pro Ala
    370                 375                 380

Ser Pro Glu Pro Pro Ala Ser Cys Arg Gly Tyr Cys Pro Trp Glu Ala
385                 390                 395                 400

Leu Met Lys Val Pro Pro Ser Leu Pro Val
                405                 410
```